United States Patent
Sisto et al.

(10) Patent No.: US 6,957,912 B2
(45) Date of Patent: Oct. 25, 2005

(54) X-RAY FILM HOLDER

(75) Inventors: Eugene Sisto, Rochester, NY (US);
Ronald A. Figler, Farmington, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/869,354

(22) Filed: Jun. 16, 2004

(65) Prior Publication Data

US 2005/0190889 A1  Sep. 1, 2005

Related U.S. Application Data

(60) Provisional application No. 60/549,355, filed on Mar. 1, 2004.

(51) Int. Cl.[7] .............................................. A61B 6/14
(52) U.S. Cl. ...................................... 378/168; 378/174
(58) Field of Search ................................ 378/168, 169, 378/170, 174, 191, 205

(56) References Cited

U.S. PATENT DOCUMENTS

| 4,251,732 A |   | 2/1981 | Fried ........................... 378/170 |
| 5,022,065 A | * | 6/1991 | Wijkstrom ................... 378/168 |
| 6,343,875 B1 | * | 2/2002 | Eppinger et al. ........... 378/170 |
| 6,612,740 B1 |   | 9/2003 | Resch et al. ................ 378/169 |

\* cited by examiner

Primary Examiner—Edward J. Glick
Assistant Examiner—Courtney Thomas
(74) Attorney, Agent, or Firm—Susan L. Parulski; Nelson Adrian Blisk

(57) ABSTRACT

An intra-oral film packet holder. The packet holder comprises an arm and a holder portion disposed at one end of the arm. The holder portion comprises a first and second receiving area adapted to receive a intra-oral film packet. Each receiving area is defined by a pair of spaced opposing grooves. The first and second receiving areas are disposed adjacent each other, substantially parallel, and of differing lengths such that the first and second receiving areas are adapted to receive intra-oral film packets of different sizes.

10 Claims, 2 Drawing Sheets

X-RAY FILM HOLDER

CROSS REFERENCE TO RELATED APPLICATION

This is a 111a application of provisionally filed U.S. Patent Application Ser. No. 60/549,355 entitled "X-RAY FILM HOLDER", filed on Mar. 1, 2004 in the names of Sisto et al., and which is incorporated herein by reference.

FIELD OF THE INVENTION

The invention relates generally to the field of x-ray imaging, and in particular to an x-ray film holder for intra-oral dental x-ray imaging.

BACKGROUND OF THE INVENTION

Dental radiographs are made using x-ray examination units to acquire x-ray images of particular teeth of a patient. More particularly, an intra-oral radiographic film packet is positioned in a holder and placed in a patient's mouth, wherein the film packet is exposed to x-rays to acquire an image of the teeth of the patient.

To position the intra-oral film packet in the patient's mouth, a holder is typically employed. Examples of dental x-ray film holders are disclosed in U.S. Pat. No. 4,251,732 (Fried), U.S. Pat. No. 5,022,065 (Wijkstrom), and U.S. Pat. No. 6,343,875 (Eppinger), all of which are incorporated herein by reference.

Intra-oral film packets are available in various sizes and shapes. For example, film packets of smaller dimensions are available for children. Intra-oral film packets also comprise various features which can affect the size shape. For example, U.S. Pat. No. 6,612,740 (Resch), commonly assigned and incorporated herein by reference, discloses a intra-oral film packet having a comfort-enhancing perimetric edge bead. The inclusion of this feature can affect the size of the film packet, and accordingly, the size of a comfort-enhanced film packet can differ from a non-enhanced film packet.

Since the intra-oral film packets can vary in size and shape, there exists a need for a secure holder of film packets which can accommodate different size and shape intra-oral film packets while providing comfort to the patient when placed in the patient's mouth.

SUMMARY OF THE INVENTION

An object of the present invention is to provide a holder for an intra-oral film packet.

Another object of the present invention is to provide such a holder which can accommodate at least two different size and shape intra-oral film packets.

Yet another object of the present invention is to provide such a holder which is hygienic.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided an intra-oral film packet holder, comprising an arm and a holder portion disposed at one end of the arm. The holder portion comprises a first and second receiving area adapted to receive a intra-oral film packet. Each receiving area is defined by a pair of spaced opposing grooves. The first and second receiving areas are disposed adjacent each other, substantially parallel, and of differing dimensions such that the first and second receiving areas are adapted to receive intra-oral film packets of different sizes.

BRIEF DESCRIPTION OF THE DRAWINGS

The foregoing and other objects, features, and advantages of the invention will be apparent from the following more particular description of the preferred embodiments of the invention, as illustrated in the accompanying drawings.

DETAILED DESCRIPTION OF THE INVENTION

Figure 1:
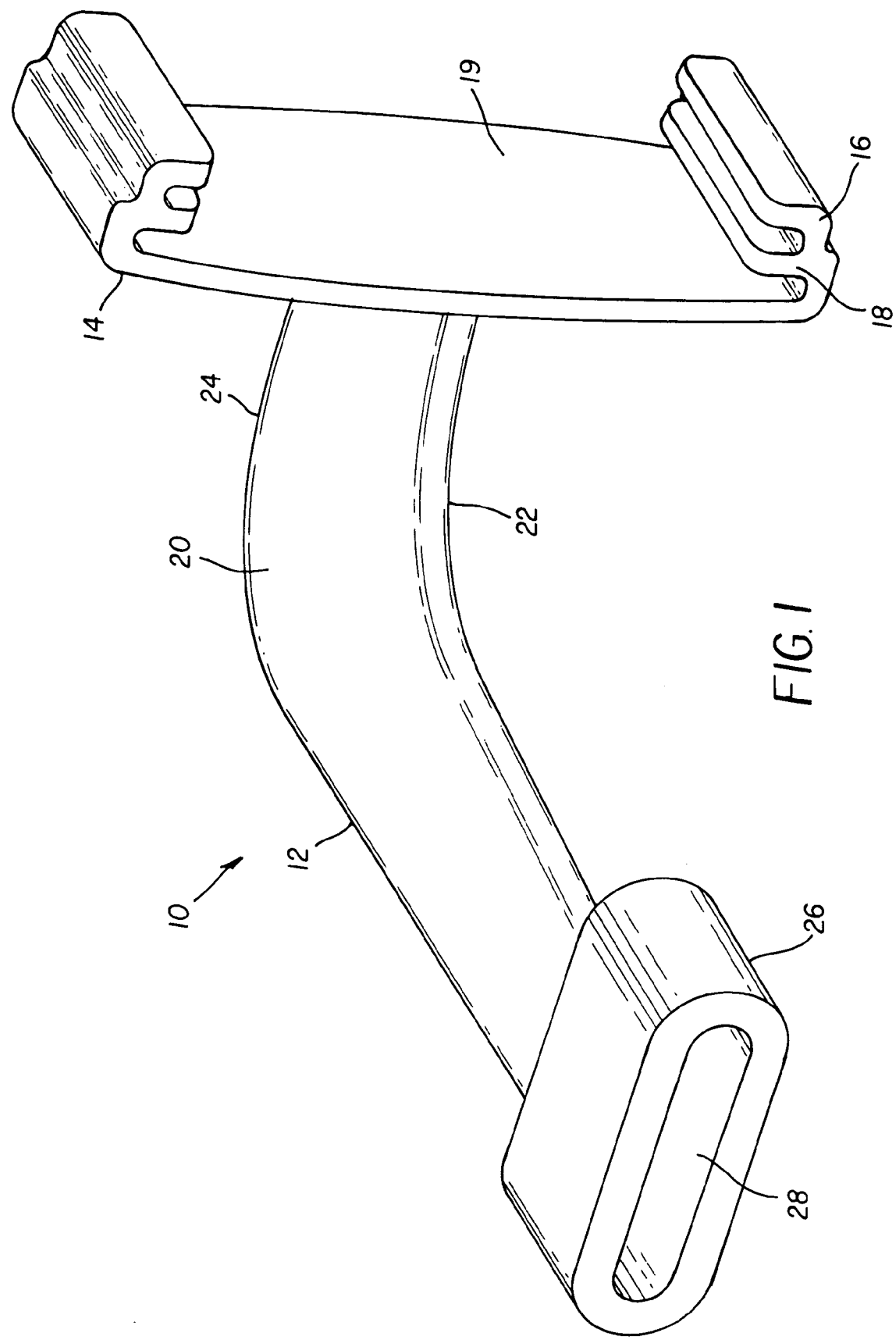
FIG. 1 shows a perspective view of a holder in accordance with the present invention.

The following is a detailed description of the preferred embodiments of the invention, reference being made to the drawings in which the same reference numerals identify the same elements of structure in each of the several figures.

Figure 2:
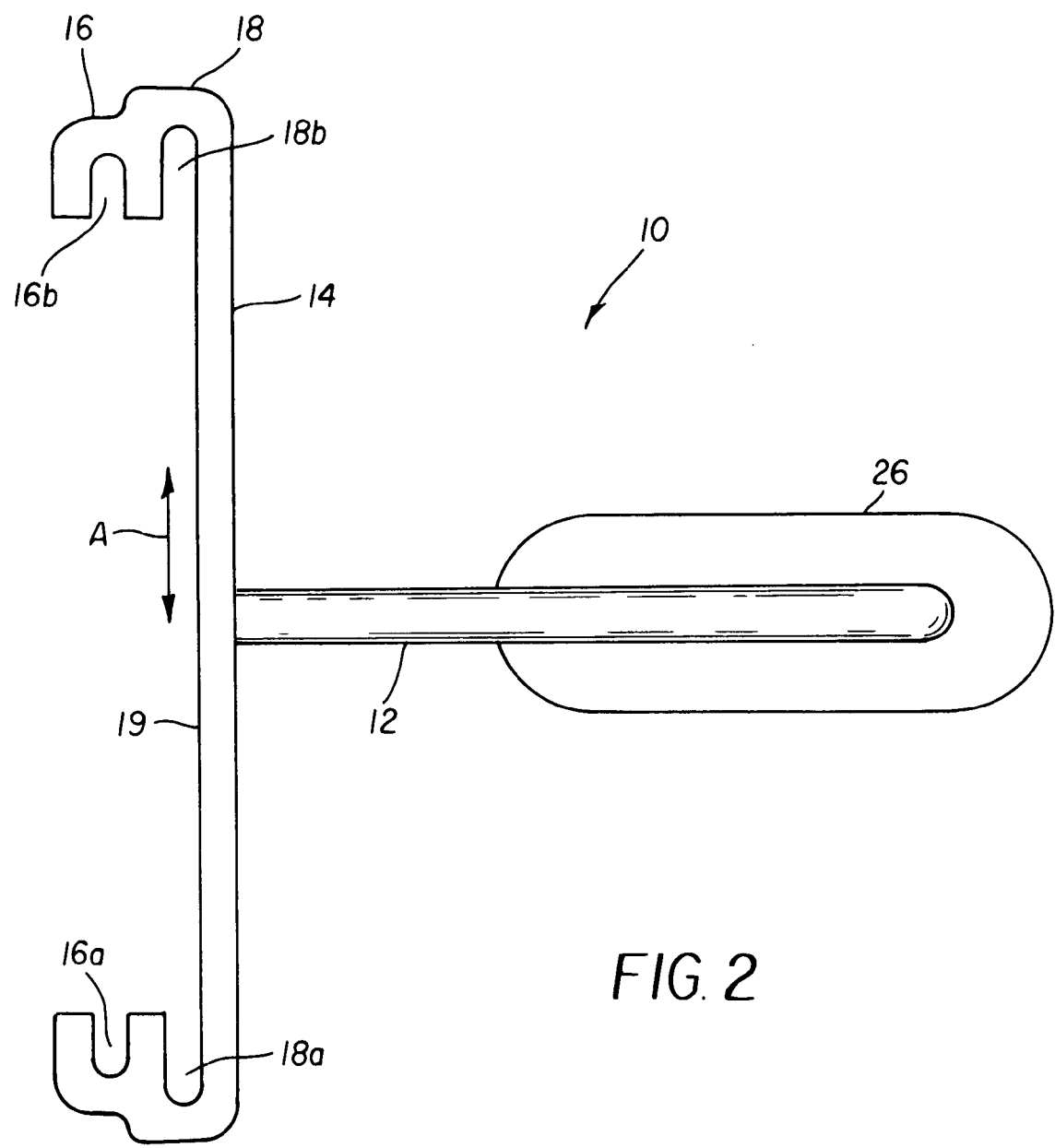
FIG. 2 shows an end view of the holder of FIG. 1.

There is shown in FIGS. 1 and 2 an intra-oral film holder 10 in accordance with the present invention. Holder 10 includes an arm/handle 12 and a holder head 14. Holder head 14 comprises at least two insertion areas or receiving areas 16,18, each adapted to receive an intra-oral film packet inserted therein wherein each receiving area of holder 10 is of a different size. Receiving areas 16,18 are disposed adjacent and substantially parallel to each other, shown in FIG. 2 by direction A. Receiving areas 16,18 are shown as each having two opposing grooves or slot portions 16a,16b, 18a,18b, respectively, which are spaced apart by an open area. Slot portions 16a,16b,18a,18b are configured to each receive one edge of an intra-oral film packet. Receiving areas 16,18 extend along a length/dimension substantially parallel to direction A (best shown in FIG. 2) and have a depth/height extending in a dimension substantially perpendicular to direction A (best shown in FIG. 1). By such an arrangement, holder 10 can securely hold the intra-oral film packet.

Receiving areas 16,18 are of different sizes so that holder 10 can be employed for use with intra-oral film packets of different sizes. For example, for Applicant's application, a film packet having a comfort-enhancing perimetric edge bead can be disposed in receiving area 18, while a film packet which does not have the edge bead can be disposed in receiving area 16. As such, a dentist can stock two types of film packets, but need only stock one holder.

Accordingly, as best shown in FIG. 2, the length/dimension of receiving areas 16,18 which extends substantially parallel to direction A is different for the two receiving areas. That is, this length/dimension is different for receiving area 16 than for receiving area 18.

Preferably, the receiving area disposed furthest from arm 12 (i.e., receiving area 16) is of a smaller size than the receiving area disposed closest arm 12 (i.e., receiving area 18). Such an arrangement is shown in FIGS. 1 and 2, wherein wall portion 19 extends substantially perpendicular to arm 12, and arm 12 is substantially disposed at the center-point/mid-point of wall portion 19 so that intra-oral film packets are centered relative to arm 12.

In a preferred embodiment, arm 12 is configured so as to extend be disposed receiving areas 16,18.

Arm 12 is preferably comprised of a substantially flat/planar portion 20 and so as to provide a biting-portion for a patient to comfortably position holder 10 in their mouth by biting on arm 12. Planar portion 20 can include a curved shape, as best shown in FIG. 1. Arm 12 includes edges 22,24.

Arm 12 can include, at an end opposite holder head 14, a connector 26 adapted to connect holder 10 to another entity. For example, as disclosed in U.S. Pat. No. 6,343,875 (Eppinger), holder 10 might be connected to a x-ray tube collimator-positioning ring employed to correctly position an x-ray source relative to the intra-oral film packet, as is well-known to those skilled in the art. Various configurations for connector 26 are known. As shown in the figures, connector 26 includes a slot 28 adapted to receive a mating device.

Arm 12 and holder head 14 are preferably a unitary element to promote connection of holder head 14 to arm 12. Connector 26 may be a separate element attachable/removable from arm 12. Preferably, arm 12, holder head 14, and connector 26 is one contiguous piece, for example as formed by molding.

Holder 10 is comprised of a material which is transparent to x-rays. In addition, since holder 10 can be exposed to a patient's mouth, holder 10 can be comprised of a material which can be autoclaved in accordance with known procedures to sterilize holder 10. However, Applicants recognized that holder 10 can be comprised of a polymeric material which is of a low cost and readily formable, and preferably recyclable. As such, holder 10 can be discarded/recycled rather than autoclaved. Suitable materials might include polypropylene.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. An intra-oral film packet holder, comprising:
   an arm;
   a holder portion disposed at one end of the arm, the holder portion comprising a first and second receiving area adapted to receive an intra-oral film packet, each receiving area defined by a pair of spaced opposing grooves, the first and second receiving areas being disposed adjacent each other, substantially parallel, and of differing dimensions such that the first and second receiving areas are adapted to receive intra-oral film packets of different sizes; and
   wherein an orientation of each intra-oral film packet with respect to a patient's teeth is the same.

2. The intra-oral film packet holder of claim 1, further comprising a connector disposed at the other end of the arm and adapted to connect the packet holder to another device.

3. The intra-oral film packet holder of claim 1, wherein a length of the first receiving area is smaller than a length of the second receiving area, and the second receiving area is disposed proximate the arm.

4. The intra-oral film packet holder of claim 3, wherein the holder portion includes a wall extending at least the length of the second receiving area, and the arm is attached to the wall at about the mid-point of the wall.

5. The intra-oral film packet holder of claim 1, wherein the second receiving area is adapted to receive an intra-oral film packet having a comfort-enhancing perimetric edge bead and the first receiving area is adapted to receive an intra-oral film packet not having a comfort-enhancing perimetric edge bead.

6. The intra-oral film packet holder of claim 1, wherein the intra-oral film packet holder is comprised of a polymer.

7. The intra-oral film packet holder of claim 1, wherein the packet holder is an unitary element.

8. The intra-oral film packet holder of claim 1, wherein the packet holder is an unitary element formed by molding.

9. The intra-oral film packet holder of claim 1, further comprising a connector adapted to connect the packet holder to a device employed for capturing an x-ray image.

10. The intra-oral film packet holder of claim 1, wherein the packet holder is comprised of a material transparent to x-rays.

* * * * *